United States Patent [19]

Fenical et al.

[11] Patent Number: 5,624,911
[45] Date of Patent: Apr. 29, 1997

[54] ETHER DERIVATIVES OF PSEUDOPTEROSIN

[75] Inventors: William H. Fenical, Del Mar; Robert S. Jacobs, Santa Barbara, both of Calif.

[73] Assignee: The Regents of the University of California, Oakland, Calif.

[21] Appl. No.: 487,859

[22] Filed: Jun. 7, 1995

[51] Int. Cl.$^6$ .......................... A61K 31/70; C07H 15/00
[52] U.S. Cl. .................. 514/33; 536/18.1; 514/25
[58] Field of Search ................. 536/18.1; 514/25, 514/33

[56] References Cited

U.S. PATENT DOCUMENTS

| 4,745,104 | 5/1988 | Jacobs et al. ................ 514/33 |
| 4,849,410 | 7/1989 | Jacobs et al. ................ 514/33 |

OTHER PUBLICATIONS

Look et al., "The pseudopterosins: anti-inflammatory and analgesic natural products from the sea whip *Pseudopterogorgia elisabethae*," *Proc. Natl. Acad. Sci. USA*, vol. 83, pp. 6238–6240, 1986.

Look et al., "The pseudopterosins: a new class of antiinflammatory and analgesic diterpene pentosides from the marine sea whip *pseudopterogorgia elisabethae* (Octocorallia)," *J. Org. Chem.* 1986, 51, 5140–5145.

Look et al., "The seco–pseudopterosins, new anti–inflammatory diterpene–glycosides from a caribbean gorgonian octocoral of the genus *pseudopterogorgia*," *Tetrahedron*, vol. 43, No. 15, pp. 3363–3370, 1987.

Roussis et al., "New antiinflammatory pseudopterosins from the marine octocoral *pseudopterogorgia elisabethae*," *J. Org. Chem.*, 1990, vol. 55, No. 16, 4916–4922.

Primary Examiner—Elli Peselev
Attorney, Agent, or Firm—Oppenheimer Poms Smith

[57] ABSTRACT

Methods for treating mammals to reduce pain and/or reduce inflammation are described based on administering to the mammals synthetic ether derivatives of pseudopterosin having the formula:

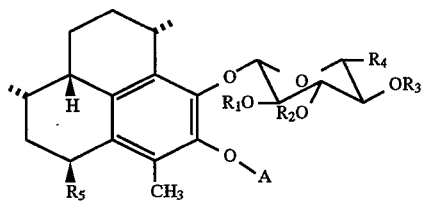

wherein A is an alkyl, aryl or amide group having from 2 to 20 carbon atoms, $R_1$, $R_2$ and $R_3$ are hydrogen or an acyl residue (—COR) having from 1 to 6 carbon atoms, $R_4$ is hydrogen or —CH$_2$OH and $R_5$ is a hydrocarbon having from 1 to 10 carbon atoms. Also disclosed are synthetic compositions having the above general formula which are useful in the described method.

35 Claims, No Drawings

ETHER DERIVATIVES OF PSEUDOPTEROSIN

This invention was made with Government support under Sea Grant No. NA 80 AA-D-00120, Project R/MP-21, R/MP-22 and R/MP-54 awarded by the California Sea Grant College Program. The Government has certain rights in this invention.

BACKGROUND OF THE INVENTION

1. Field of the Invention

The present invention relates generally to synthetic derivatives of pseudopterosin and their use in the treatment of inflammation and pain. More particularly, the present invention involves the discovery that certain specific ether derivatives of pseudopterosin are useful pharmaceutical agents which are especially effective in reducing inflammation and pain.

2. Description of Related Art

Caribbean gorgonians (*O. gorgonacea, Ph. cnidaria*) are a diverse group of marine animals which are commonly known as sea whips and sea fans. A wide variety of Caribbean gorgonians are found in abundance in the shallow-water reefs of the West Indian region. A few of the Caribbean gorgonians have been analyzed for their chemical content and found to be a source of many diverse organic substances such as steroids, prostaglandins, lactones, sesquiterpenoid derivatives and diterpenoid metabolites. Some of these substances have been found to be biologically active.

Since only a small percentage of the total number of Caribbean gorgonian species have been examined for natural chemical products, there has been a continuing effort by a number of researchers to examine additional gorgonian species in order to isolate possible novel natural chemical compounds. Pseudopterogorgia is one type of gorgonian that has been studied extensively in an effort to isolate and identify potentially useful pharmacologically active compounds. As a result of this effort, a group of naturally occurring diterpenoid glycosides have been isolated and identified. This isolated group of diterpenoid glycosides are commonly referred to as pseudopterosins. Over ten different pseudopterosins have been isolated from Pseudopterogorgia. Only a few of these naturally occurring pseudopterosins have been shown to have pharmaceutical activity. These active pseudopterosins have been used exclusively as anti-inflammatory and/or analgesic agents.

In addition to the naturally occurring pseudopterosins, a number of synthetic pseudopterosin derivatives have been prepared. Some of these synthetic pseudopterosins were also found to be pharmacologically active. They are described in U.S. Pat. Nos. 4,745,104 and 4,849,410 which were issued on May 17, 1988 and Jul. 18, 1989, respectively. These two patents are owned by the same assignee as the present invention.

SUMMARY OF THE INVENTION

In accordance with the present invention, it was discovered that certain synthetic ether derivatives of pseudopterosin are effective anti-inflammatory and analgesic agents. The ether derivatives have the formula:

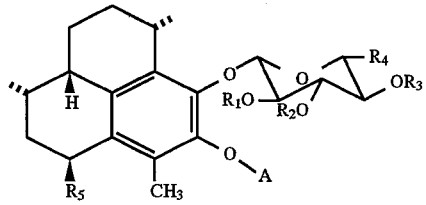

wherein A is an alkyl, aryl or amide group having from 2 to 20 carbon atoms, $R_1$, $R_2$ and $R_3$ are hydrogen or an acyl residue having from 1 to 6 carbon atoms, $R_4$ is a hydrogen or $CH_2OH$ and $R_5$ is an organo group having from 1 to 10 carbon atoms.

The ether derivatives in accordance with the present invention are effective in treating both inflammation and pain. The ether derivatives are also stable. As a result, they are resistant to in vivo metabolization and consequently remain active during treatment involving in vivo administration. The stability of the ether derivatives also provides the added benefit of increasing the shelf life of the pharmaceutical preparations in which they are incorporated.

The ether derivatives are useful in treating the same types of inflammatory disorders which have been treated using other pseudopterosins. In addition, the ether derivatives are useful in treating inflammatory diseases of the lungs including emphysema and chronic inflammation due to smoking. The ether derivatives are also useful in treating degenerative diseases associated with radiation exposure. The ether derivatives have also been found to be effective in treating cartilage and other connective tissue which has been degraded by arthritis or other degenerative disease.

The present invention includes methods for treating mammals to reduce inflammation and/or pain wherein an ether derivative of pseudopterosin having the formula set forth above is administered to mammals. The ether derivatives are administered in the same manner as other known anti-inflammation and analgesic agents.

The present invention also includes compositions for use as anti-inflammatory agents and analgesic agents which comprise an effective amount of one or more of the above-identified ether derivatives of pseudopterosin and a pharmaceutically acceptable carrier.

The above discussed and many other features and attendant advantages of the present invention will become apparent as the invention becomes better understood by reference to the following detailed description.

DETAILED DESCRIPTION OF THE INVENTION

The ether derivatives of pseudopterosin employed in the compositions and methods of the present invention may be represented by the formula:

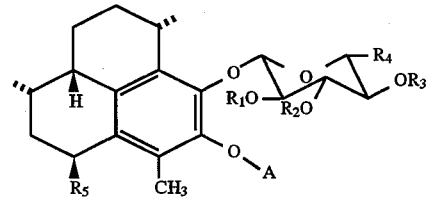

wherein A is an alkyl, aryl or amide group having from 2 to 20 carbon atoms, $R_1$, $R_2$ and $R_3$ are hydrogen or an acyl residue (—C(O)R) having from 1 to 6 carbon atoms, $R_4$ is a hydrogen or $CH_2OH$ and $R_5$ is an organo group having from 1 to 10 carbon atoms.

Exemplary preferred ether derivatives are straight chain alkyl ethers where A=—$(CH_2)_n$ $CH_3$ and where n=1 to 19. Straight chain alcohol ethers are also suitable where A=—$(CH_2)_n$ $CH_2$—OH and where n=1 to 19. Amide ethers of pseudopterosin which are suitable in accordance with the present invention include those where A=—$(CH_2)_n$ $CONH_2$ where n=1 to 19. Phenyl ethers are also possible where A=—$(CH_2)_n$—phenyl and n=1 to 14. It is preferred for all of the above derivatives that $R_1$, $R_2$, $R_3$ and $R_4$=H and that $R_5$=2-methyl-1-propene.

Specific exemplary ethers are those where:

| | |
|---|---|
| 1 A = —$CH_2$-Phenyl; $R_1$, $R_2$, $R_3$, $R_4$ = H; and $R_5$ = 2-methyl-1-7 propene ($C_{32}H_{42}O_6$; MW 522) | (WF-332) |
| 2 A = —$(CH_2)_4CH_3$; $R_1$, $R_2$, $R_3$, $R_4$ = H; and $R_5$ = 2-methyl-1-7 propene ($C_{30}H_{46}O_6$ MW 502) | (WF-333) |
| 3 A = —$(CH_2)_9CH_3$; $R_1$, $R_2$, $R_3$, $R_4$ = H; and $R_5$ = 2-methyl-1-7 propene ($C_{35}H_{56}O_6$; MW 572) | (WF-334) |
| 4 R = —$(CH_2)_{17}CH_3$; $R_1$, $R_2$, $R_3$, $R_4$ = H; and $R_5$ = 2-methyl-1-7 propene ($C_{43}H_{72}O_6$; MW 684) | (WF-335) |
| 5 R = —$(CH_2)_3$ $CH_2$—OH; $R_1$, $R_2$, $R_3$, $R_4$ = H; and $R_5$ = 2-methyl-1-7 propene ($C_{29}H_{44}O_7$; MW 504) | (WF-336) |
| 6 R = —$CH_2$ $CONH_2$; $R_1$, $R_2$, $R_3$, $R_4$ = H; and $R_5$ = 2-methyl-1-7 propene ($C_{27}H_{39}O_7N$; MW 490) | (WF-337) |

Other preferred ethers include those where A is cycloalkyl, cycloalkenyl, —$(CH_2)_n$—COOH where n=1 to 19, —$(CH_2)_n$—$NH_2$ where n=1 to 20; $R_1$, $R_2$, $R_3$, $R_4$=H; and $R_5$=2-methyl-1-propene.

The $R_1$, $R_2$ and $R_3$ groups are preferably hydrogen or acetate. In preferred compounds, all three positions are hydrogen. Other exemplary groups which may be attached at the $R_1$, $R_2$ and $R_3$ positions are acyl groups having from 1 to 6 carbon atoms.

Groups which may be attached at $R_4$ are hydrogen (when a pentose sugar moiety is desired) or $CH_3$ or $CH_2OH$ (when a hexose sugar is desired).

Exemplary groups which may be attached at the $R_5$ position are alkanes, alkenes or alkynes having from 1 to 10 carbon atoms. Other exemplary groups are alcohols, aldehydes, epoxides, ketones, acids or other solubility modifying groups as part of an alkyl residue of from 4 to 10 carbon units. Preferably, $R_5$ is a propene derivative. Alternatively, $R_3$ is preferably a propane derivative. Most preferably, $R_6$ is 2-methyl-1-propene.

The pseudopterosin ether derivatives in accordance with the present invention may be synthesized by derivatizing the various different naturally occurring pseudopterosin compounds which are isolated from sea whips according to known procedures. The following references set forth the procedures which may be used to isolate naturally occurring pseudopterosin: Look et al., *Proc. Natl. Acad. Sci. USA*, 1986, 83:6238–6240; Look et al., *J. Org. Chem.*, 1986, 51:5140–5145; Look et al., *Tetrahedron*, 1987, 43:3363–3370; Roussis et al., *J. Org. Chem.*, 1990, 55:4916–4922; and U.S. Pat. Nos. 4,849,410 and 4,745,104.

The procedures for substituting the various different R groups into the pseudopterosin compounds are conventional in nature and involve substitution of A to form ether derivatives, substitution of $R_1$-$R_3$ groups either on a ribose ($R_4$=hydrogen) or hexose ($R_4$=$CH_3$ or $CH_2OH$) moiety or substitution of the $R_5$ group on the tricarbocyclic diterpene structure.

Exemplary synthesis of the ether derivatives of pseudopterosin-A are as follows:

1. Synthesis of Pseudopterosin A Benzyl ether (WF-332)

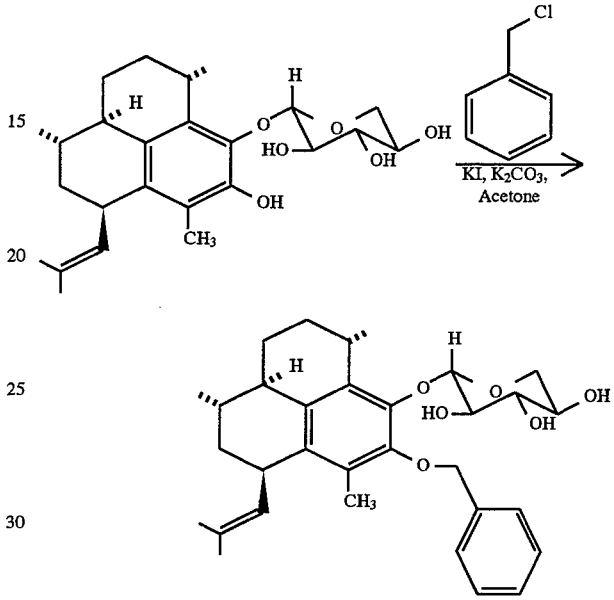

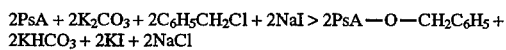

2PsA + 2$K_2CO_3$ + 2$C_6H_5CH_2Cl$ + 2NaI > 2PsA—O—$CH_2C_6H_5$ + 2$KHCO_3$ + 2KI + 2NaCl

Preparation:

Pseudopterosin A (150 mg in 50 ml acetone) was placed in a 100 ml flask. $K_2CO_3$ (150 mg), sodium iodide (500 mg) and benzylchlorine (1.1 g=1 ml) were added. The solution was stirred and refluxed for 5 hours. After stirring overnight, 0.5 ml benzylchloride was added and the solution was refluxed for another 6 hours. After cooling to room temperature, the yellow solution was concentrated by rotary evaporation. Water (50 ml) and $CH_2Cl_2$ (30 ml) were added to the concentrate and the solution was transferred to a separatory funnel and extracted 3 times with $CH_2Cl_2$ (3×50 ml). The total collected $CH_2Cl_2$ layers were washed with brine (3×50 ml). Next, the solution was transferred to an Erlenmeyer flask and dried with $Na_2SO_4$. The dry solution was filtered and concentrated under vacuum to give a yellow oil.

Purification:

For purification, the yellow oil was chromatographed on a silica column eluting with 65/35 ethyl acetate/isooctane. The product was dried under high vacuum to give white crystals. Yield: 90 mg=50%.

Synthesis of Pseudopterosin A Pentyl ether (WF-333)

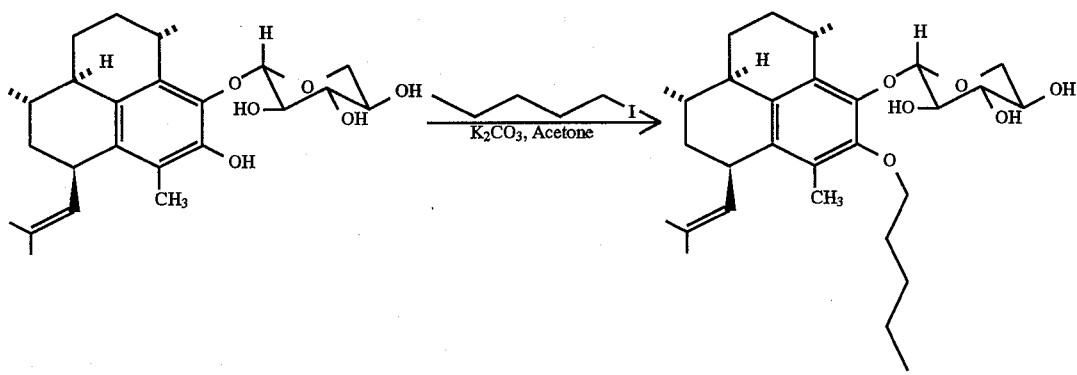

PsA + K₂CO₃ + CH₃(CH₂)₄I > PsA—O—(CH₂)₄CH₃ + KHCO₃ + KI

Preparation:

Pseudopterosin A (150 mg in 70 ml acetone) was placed in a 100 ml flask. K₂CO₃ (150 mg) and 1-iodopentane (1400 mg=0.92 ml) were added. The solution was stirred and refluxed overnight. After cooling to room temperature, the solution was concentrated by rotary evaporation. Water (30 ml) and CH₂Cl₂ (30 ml) were added to the concentrate and the solution was transferred to a separatory funnel and extracted 3 times with CH₂Cl₂ (3×30 ml). The total collected CH₂Cl₂ layers were washed with brine (3×50 ml). Next, the solution was transferred to an Erlenmeyer flask and dried with Na₂SO₄. The dry solution was filtered and concentrated under vacuum to give a yellow oil.

Purification:

For purification, the yellow oil was chromatographed on a silica column eluting with 50/50 ethyl acetate/isooctane. The product was dried under high vacuum to give white crystals. Yield: 84 mg=49%.

3. Synthesis of Pseudopterosin A Decanyl ether (WF-334)

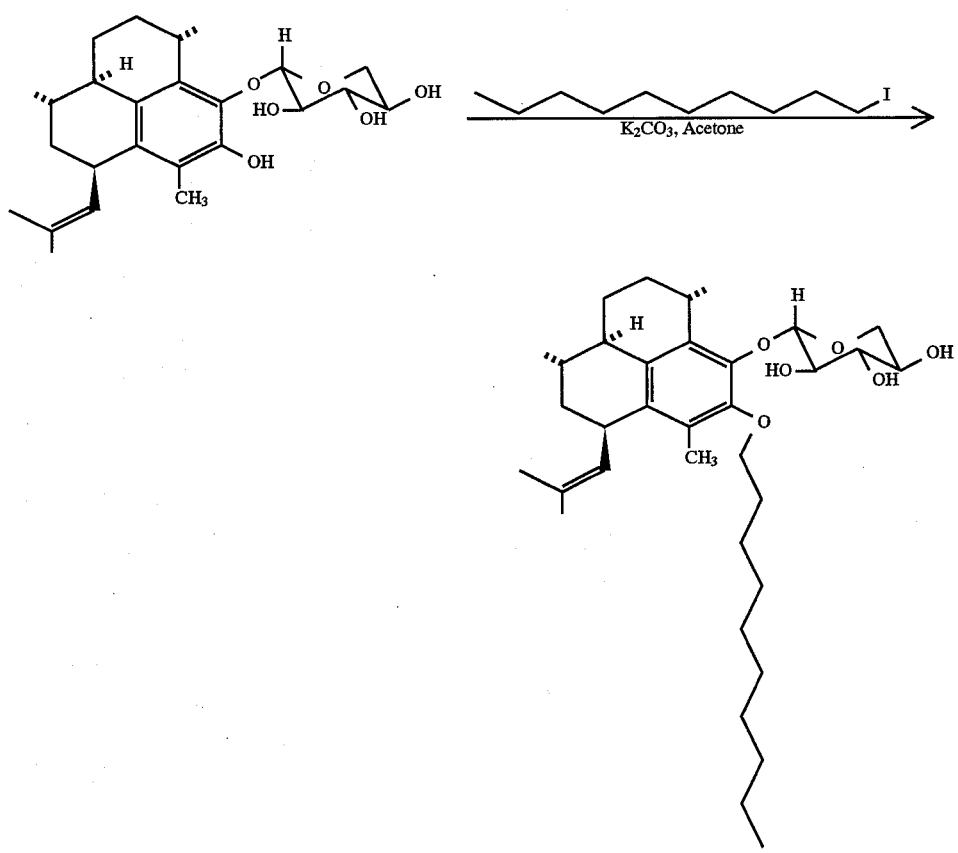

PsA + K₂CO₃ + CH₃(CH₂)₉I > PsA—O—CH₂(CH₂)₈CH₃ + KHCO₃ + KI

Pseudopterosin A (150 mg in 100 ml acetone) was placed in a 250 ml flask. K₂CO₃ (150 mg) and 1-iododecane (930 mg=0.74 ml) were added. The solution was stirred and refluxed for 5 hours. After stirring overnight, 0.74 ml 1-iododecane and 150 mg K₂CO₃ were added again and the solution was refluxed for another 15 hours. After cooling to room temperature, the solution was concentrated by rotary evaporation. Water (50 ml) and $CH_2Cl_2$ (50 ml) were added to the concentrate and the solution was transferred in a separatory funnel and extracted 3 times with $CH_2Cl_2$ (3×75 ml). The total collected $CH_2Cl_2$ layers were washed with brine (3×50 ml). Next, the solution was transferred to an Erlenmeyer flask and dried with $Na_2SO_4$. The dry solution was filtered and concentrated under vacuum to give a yellow oil.

Purification:

For purification, the yellow oil was chromatographed on a silica column eluting with 50/50 ethyl acetate/isooctane. The product was dried under high vacuum to give white crystals. Yield: 105 mg=52%.

4. Synthesis of Pseudopterosin A Octadecanyl ether (WF-335)

added, and the solution was stirred and refluxed for another 5 hours. After cooling to room temperature, the solution was concentrated by rotary evaporation. Water (50 ml) and $CH_2Cl_2$ (30 ml) were added to the concentrate and the solution was transferred in a separatory funnel and extracted 3 times with $CH_2Cl_2$ (3×50 ml). The total collected $CH_2Cl_2$ layers were washed with brine (3×50 ml). Next, the solution was transferred into an Erlenmeyer flask and dried with $Na_2SO_4$. The dry solution was filtered and concentrated by rotary evaporation to give a yellow oil.

Purification:

For purification, the yellow oil was chromatographed on a silica column eluting with 40/60 ethyl acetate/isooctane. The product was dried under high vacuum to give white crystals. Yield: 100 mg=42%.

5. Synthesis of Pseudopterosin A Butanol ether (WF-336)

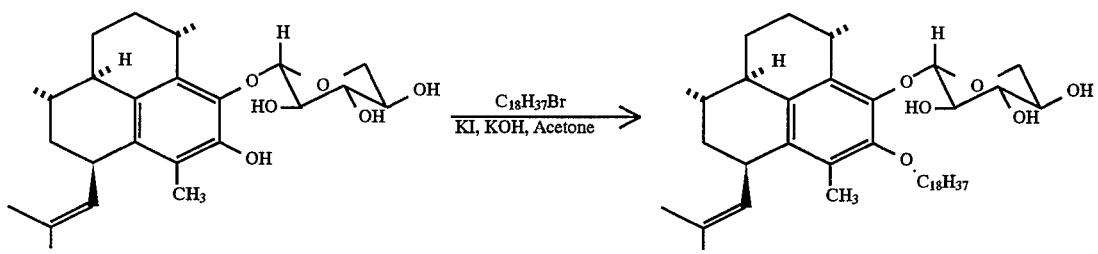

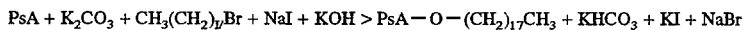

PsA + $K_2CO_3$ + $CH_3(CH_2)_{17}Br$ + NaI + KOH > PsA—O—$(CH_2)_{17}CH_3$ + $KHCO_3$ + KI + NaBr

Pseudopterosin A (150 mg in 70 ml acetone) was placed in a 100 ml flask. $K_2CO_3$ (1150 mg), sodium iodide (580 mg) and 1-bromooctadecane (2300 mg) were added. The solution was stirred and refluxed overnight. After adding 25 ml toluene, the solution was again placed in a 100 ml flask. $K_2CO_3$ (1150 mg), sodium iodide (580 mg) and 1-bromooctadecane (2300 mg) were added. The solution was stirred and refluxed overnight. After adding 25 ml toluene, the solution was again stirred and refluxed overnight. Next, 2.5 ml water and 1000 mg of $K_2CO_3$ were

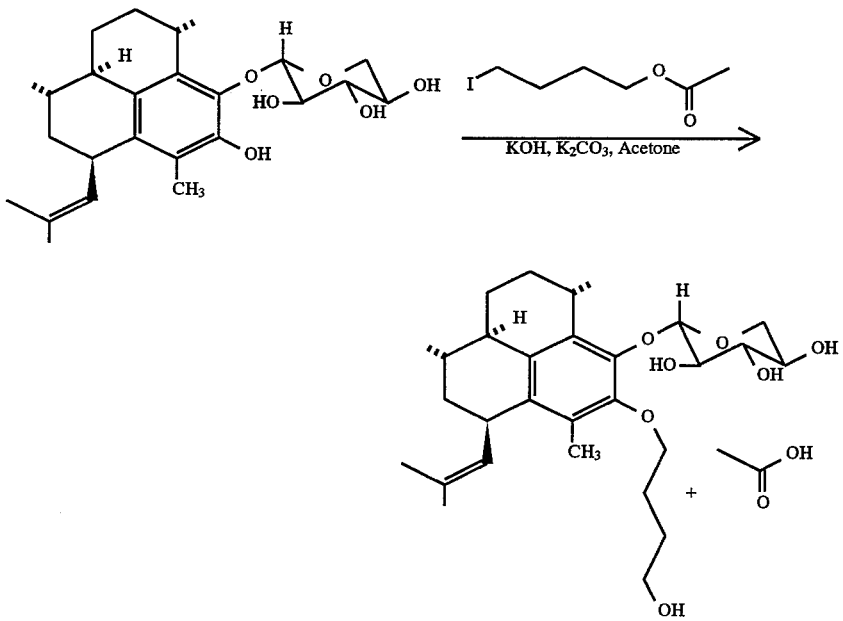

PsA + KOH + $I(CH_2)_3OOCCH_3$ > PsA—O—$(CH_2)_3OH$ + $CH_3COOH$ + KI

Preparation:

Pseudopterosin A (150 mg in 50 ml acetone) was placed in a 100 ml flask. $K_2CO_3$ (150 mg) and 4-iodobutyl acetate (1300 mg=0.8 ml) were added. The solution was stirred and refluxed overnight. Then, iodobutyl acetate (650 mg=0.4 ml) and water (2.5 ml) were added and the solution was stirred and refluxed for another 5 hours. Then, 600 mg of KOH were added, and the solution was concentrated by rotary evaporation. Water (50 ml) and $CH_2Cl_2$ (30 ml) were added to the concentrate and the solution was transferred in a separatory funnel and extracted 3 times with $CH_2Cl_2$ (3×50 ml). The total collected $CH_2Cl_2$ layers were washed with brine (3×50 ml). Next, the solution was transferred to an Erlenmeyer flask and dried with $Na_2SO_4$. The dry solution was filtered and concentrated under vacuum to give a yellow oil.

Purification:

For purification, the yellow oil was chromatographed on a silica column eluting with 65/35 ethyl acetate/isooctane. The product was dried under high vacuum to give white crystals. The product was not the expected PsA acetoxy butyl ether but the PsA butanol ether, derived by saponification of the acetate under the basic conditions employed in the reaction. Yield: 46 mg=26%.

Synthesis of Pseudopterosin A Acetamide ether (WF-337)

The ether derivatives in accordance with the present invention are useful for treating inflammation and pain. The ether derivatives may be used in the same manner as pseudopterosin A and other related anti-inflammatory and analgesic agents. The ether derivatives are effective for both topical application and in vivo use.

Pharmaceutical compositions which contain ether derivatives of pseudopterosins in accordance with the present invention are useful in the treatment of rheumatoid arthritis, osteoarthritis, rheumatic carditis, collagen and/or autoimmune diseases such as myasthenia gravis, allergic diseases, bronchial asthma and ocular and skin inflammatory diseases such as poison ivy. The compositions are also useful in treating proliferative diseases such as psoriasis.

The compositions are also useful as adjuvant therapy associated with organ and tissue transplants and any neurological disease involving metabolism of nervous tissue phospholipid such as multiple sclerosis. Because of their selective antagonism of chemical irritation (i.e., PMA inflammation) the compositions can be useful in the treatment of insect bites, bee or wasp stings or any venom in which a major constituent is the enzyme phospholipase $A_2$. The compositions are potent non-narcotic analgesics and may be used to alleviate pain resulting from traumatic injury or acute progressive disease, such as post operative pain, burns, or other conditions involving a coincident inflammation.

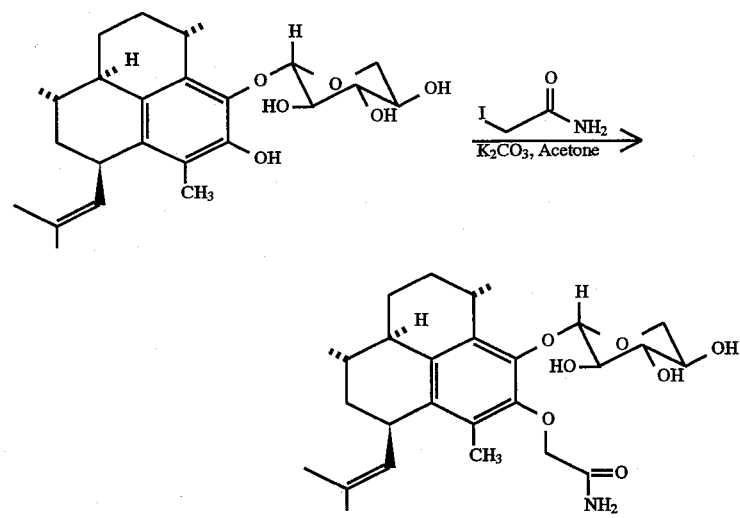

$PsA + K_2CO_3 + ICH_2CONH_2 > PsA-O-CH_2CONH_2 + KHCO_3 + KI$

Preparation:

Pseudopterosin A (150 mg in 50 ml acetone) was placed in a 100 ml flask. $K_2CO_3$ (1500 mg) and iodoacetamide (960 mg) were added. The solution was stirred and refluxed for 5 hours. After cooling to room temperature, the yellow solution was concentrated by rotary evaporation. Water (50 ml) and $CH_2Cl_2$ (30 ml) were then added to the concentrate and the solution was transferred in a separatory funnel and extracted 3 times With $CH_2Cl_2$ (3×50 ml). The total collected $CH_2Cl_2$ layers were washed with brine (3×50 ml). Next, the solution was transferred into an Erlenmeyer flask and dried with $Na_2SO_4$. The dry solution was filtered and concentrated under vacuum to give a yellow oil.

Purification:

For purification, the yellow oil was chromatographed on a silica column eluting with 97/3 ethyl acetate/isooctane, The product was dried under high vacuum to give white crystals. Yield: 67 mg=40%.

Utility of Ether Derivatives

The ether derivatives of pseudopterosin in accordance with the present invention are administered to mammals including humans in an effective amount on the order of 10 to 50 mg per day per kilogram of body weight. The drug may be administered orally, parenterally, topically or by other standard administration routes. For topical administration, any of the well-known lotions or other solutions typically used as a carrier for anti-inflammatory and analgesic agent may be used. For oral administration, the dosage form may be by tablet containing normal acceptable additives, excipients, etc. The parenteral form contains typical aqueous intravenous solution ingredients such as propylene glycol, dextrose and physiological saline or other suitable lipid solubilizing carrier.

The analgesic and anti-inflammatory properties of pseudopterosin A-methyl ether are demonstrated in the following well known pharmacological efficacy studies:

I. Mouse Ear Edema Assay

The pseudopterosin ethers were topically applied in acetone to the inside pinnae of the ears of mice in a solution containing the edema-causing irritant, phorbol 12-myristate 13-acetate (PMA). PMA alone (2 μg/ear) or in combination with 50 μg/ear of test compound was applied to the left ears (5 mice per treatment group) and acetone is applied to all right ears. After 3 hours 20 minutes incubation, the mice were sacrificed, the ears removed, and bores taken and weighed. Edema was measured by subtracting the weight of the right ear (acetone control) from the weight of the left ear (treated). Results were recorded as percent decrease (inhibition) or percent increase (potentiation) in edema relative to the PMA control group edema.

The results of the assay for ether derivatives WF332 - WF337 are set forth in TABLE 1.

TABLE 1

| Compound | Mean Edema (mgs ± SEM) | N | % Inhibition |
| --- | --- | --- | --- |
| Controls | 17.7 ± 0.6 | 15 | |
| WF 332 | 5.6 ± 1.0 | 9 | 68.3 |
| WF 333 | 6.7 ± 1.0 | 10 | 62.2 |
| WF 334 | 7.0 ± 0.9 | 10 | 60.7 |
| WF 335 | 8.0 ± 1.2 | 9 | 54.4 |
| WF 336 | 5.3 ± 0.9 | 10 | 69.9 |
| WF 337 | 8.4 ± 1.4 | 9 | 52.6 |
| WF 338 | 16.5 ± 1.2 | 8 | 6.7 |

Compound WF-338 is the bis pseudopterosin A pentanyl diether (A=$(CH_2)_5$-PsA; $R_1$, $R_2$, $R_3$, $R_4$=H; and $R_5$=2-methyl-1-propene) which was found to have little if any anti-inflammatory activity and is included for comparison purposes.

The ether derivatives were also tested to determine their usefulness in inhibiting degradation of cartilage. Bovine articular cartilage explants labeled with $^{35}$Sulfate were used to monitor chondrocyte-mediated cartilage degradation in the presence of plasminogen, at concentrations similar to that measured in synovial fluid (0.4 μM), cartilage is extremely sensitive to the effects of IL-1-stimulated degradation. Stimulated chondrocytes produce and activate plasminogen activator (uPA), causing conversion of plasminogen to plasmin. Plasmin is not only an effective activator of the MMP's, but also an effective proteoglycanase. Inhibitors were added to the assay concomitant with the cytokine IL-1, and their effect was monitored by measuring differences in $^{35}$S glycosaminoglycan release, as compared to appropriate controls.

MATERIALS AND METHODS

Plasminogen (from human plasma) was obtained from Athens Research and Technology, Athens, Ga. Recombinant Human Interleukin-1-α was obtained from R&D Systems, Minneapolis, Minn. DMEM was obtained from Gibco, Grand Island, New York. $^{35}$S-Sodium Sulfate was obtained from Amersham, Arlington Heights, Ill.

Preparation of Explants

Bovine (calf) radiocarpal joints were acquired from a local abbatoir immediately after sacrifice and transported on ice. The joints were then washed thoroughly and placed in ice containing approximately 25% Povidine (10% Povidone-Iodine topical solution). The joints were then dissected in a sterile hood using good sterile technique. Media (DMEM containing 4.5 g/L D-Glucose and L-Glutamine, without sodium pyruvate) was supplemented with HEPES buffer and sodium bicarbonate, and the pH adjusted to 7.4. The media was further supplemented with penicillin and streptomycin (100 units/mL and 100 μg/ml, respectively) and 50 μg/mL L-ascorbic acid. The cartilage surfaces were exposed, and the synovial fluid was wiped away with sterile gauze. A sterile cork-borer with a diameter of 3.5 millimeters was used to remove uniform plugs of cartilage. Proper orientation was maintained by distinguishing the underlying bony layer in the plugs (only the articulating surface of the cartilage plugs were used in the experiments). The plugs were placed in a sterile flask, washed four times with 50 mL of fresh media, and then placed in an incubator (37 degrees centigrade, with 5% $CO_2$/95% air, with adequate humidity) and allowed to equilibrate for 1 hour. A 1 mm thick slice of the articulating surface was sliced off of each individual cartilage plug, using a specially designed template to obtain uniform thickness. The cartilage disks were then labeled en mass with $^{35}$Sulfate at a concentration of approximately 10 μCi/mL for approximately 72–96 hours, with hand-stirring every few hours. Subsequent to labeling, explants were equilibrated with fresh media each 48 hours. The total time for labeling/equilibration was approximately one week from acquisition/dissection of tissue. It is important to allow this slow equilibration, to achieve explants which demonstrate a smaller background, thereby giving a more sensitive assay.

Inhibition of IL-1-induced Cartilage Degradation in the Presence of Human Plasminogen For testing of ether derivatives, individual explants were transferred to 96-well plates containing 250μL of media with or without Plasminogen plus IL-1, and with or without ether derivative. For example, a negative control consists of media alone, while the two positive controls are IL-1 alone, and Plasminogen plus IL-1 (a plasminogen control was not considered necessary, since it gave the same results as media alone). All other groups in any assay would contain ether derivative along with concomitant plasminogen plus IL-1. Five samples were routinely used, with concentrations of plasminogen plus IL-1 of 0.4 μM and 0.5 ng/mL, respectively. The assay is allowed to incubate for 96 hours, prior to counting a 50 μL sample of supernatant from each well. A 50 μL sample of a papain digest of each explant is also counted for each respective well. From the counts released into the supernatant over four days, and the total counts present, the data can be expressed as % glycosaminoglycan (GAG) over the four days). The media alone % GAG release values are subtracted from all other values where plasminogen plus IL-1 were present (media alone represents the background for the system). All groups with inhibitor present are then compared to the values for the plasminogen plus IL-1 without inhibitor, and a % inhibition is calculated.

Results

Interleukin-1 mediated cartilage degradation. Human recombinant Interleukin-1-α induces degradation in bovine articular cartilage explants in a dose-dependent manner. Control explants, without IL-1-α, always displays a basal release less than or equal to 10% of the total glycosaminoglycan (GAG) pool labeled with $^{35}$Sulfate. IL-1-α at a concentration of 2.5 ng/mL initiates a two-fold increase in degradation over control. At 10 ng/mL there is approximately a 35% release of $^{35}$S-labeled GAG.

Interleukin-1 mediated cartilage degradation in the presence of 0.4 μM plasminogen. Addition of 0.4 μM human plasminogen alone to the cartilage explants does not induce any degradation above control levels. With 1 ng/mL of IL-1-α plus 0.5 μM plasminogen, nearly complete GAG degradation was observed, with greater than 90% GAG release. At lower concentrations of IL-1-α plus plasminogen, 0.4 ng/mL and 0.4 μM respectively, approximately 50% $^{35}$S-GAG release occurred over a four day assay. We chose to use the latter concentrations of IL-1-α plus plasminogen for our studies, since they represented submaximal stimulation, and gave consistent reproducible results in the assessment of efficacy of inhibitors.

13

The results of the assay are set forth in TABLE 2.

TABLE 2

| | % Inhibition @ 30 μM (Explant) | IC50 (μM) |
|---|---|---|
| WF 332 | 57 | 26 |
| WF 333 | 58 | >40 |
| WF 334 | Inconclusive | Inconclusive |
| WF 335 | 27 | >30 |
| WF 336 | 73 | 19 |
| WF 337 | 74 | 15 |
| WF 338 | 0 | >30 |

As can be seen from TABLE 2, the ether derivatives all inhibited explant degradation, except for WF 338 which is the bis pseudopterosin A pentanyl diether which has been included for comparison purposes.

Having thus described exemplary embodiments of the present invention, it should be noted by those skilled in the art that the within disclosures are exemplary only and that various other alternatives, adaptations and modifications may be made within the scope of the present invention. Accordingly, the present invention is not limited to the specific embodiments as illustrated herein, but is only limited by the following claims.

What is claimed is:

1. A compound having the chemical formula:

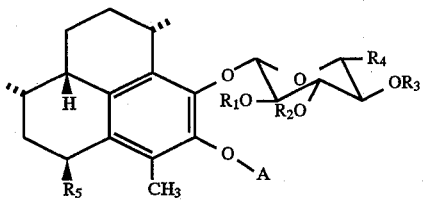

wherein A is an alkyl, aryl, hydroxyalkyl, cycloalkyl, cycloakenyl, carboxylic acid, alkylamino or amide group having from 2 to 20 carbon atoms, $R_1$, $R_2$ and $R_3$ are hydrogen or acyl residue having from 1 to 6 carbon atoms, $R_4$ is a hydrogen or $CH_2OH$ and $R_5$ is an organo group having from 1 to 10 carbon atoms.

2. A compound according to claim 1 wherein A=—$(CH_2)_n$ $CH_3$ where n=1 to 19.

3. A compound according to claim 2 wherein $R_5$=2-methyl-1-propene.

4. A compound according to claim 3 wherein $R_1$, $R_2$, $R_3$ and $R_4$ are hydrogen.

5. A compound according to claim 1 wherein A=—$(CH_2)_n$ $CH_2$—OH where n=1 to 19.

6. A compound according to claim 5 wherein $R_5$ is 2-methyl-1-propene. methyl-1 -propene.

7. A compound according to claim 6 wherein $R_1$, $R_2$, $R_3$ and $R_4$ are hydrogen.

8. A compound according to claim 1 wherein A=—$(CH_2)_n$ $CONH_2$ where n=1 to 19.

9. A compound according to claim 8 wherein $R_5$ is 2-methyl-1-propene.

10. A compound according to claim 9 wherein $R_1$, $R_2$, $R_3$ and $R_4$ are hydrogen.

11. A compound according to claim 1 wherein A=$(CH_2)_n$-phenyl where n=1–14.

12. A compound according to claim 11 wherein $R_5$ is 2-methyl-1-propene.

13. A compound according to claim 12 where $R_1$, $R_2$, $R_3$ and $R_4$ are H.

14. A compound according to claim 1 wherein A=cycloalkyl.

14

15. A compound according to claim 1 wherein A=cycloakenyl.

16. A compound according to claim 1 wherein A=—$(CH_2)_n$—COOH where n=1–19.

17. A compound according to claim 1 wherein A=—$(CH_2)_n$—$NH_2$ where n=20.

18. A composition for use as an anti-inflammatory or analgesic agent in treating mammals, said composition comprising an effective amount of an ether derivative of pseudopterosin having the structure:

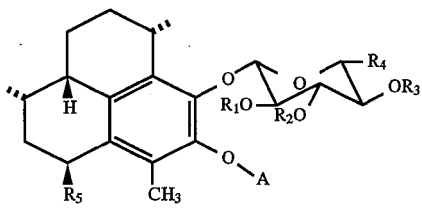

wherein A is an alkyl, aryl, hydroxyalkyl, cycloalkyl, cycloalkenyl, carboxylic acid, alkylamino or amide group having from 2 to 20 carbon atoms, $R_1$, $R_2$ and $R_3$ are hydrogen or an acyl residue having from 1 to 6 carbon atoms, $R_4$ is a hydrogen or $CH_2OH$ and $R_5$ is an organo group having from 1 to 10 carbon atoms;

and a pharmaceutically acceptable carrier for said ether derivative of pseudopterosin.

19. A composition according to claim 18 wherein A=—$(CH_2)_n$ $CH_3$ where n=1 to 19.

20. A composition according to claim 19 wherein $R_5$=2-methyl-1-propene.

21. A composition according to claim 20 wherein $R_1$, $R_2$, $R_3$ and $R_4$ are hydrogen.

22. A composition according to claim 18 wherein A=—$(CH_2)_n$ $CH_2$—OH where n=1 to 19.

23. A composition according to claim 22 wherein $R_5$ is 2-methyl-1-propene.

24. A composition according to claim 23 wherein $R_1$, $R_2$, $R_3$ and $R_4$ are hydrogen.

25. A composition according to claim 18 wherein A=—$(CH_2)_n$ $CONH_2$ where n=1 to 19.

26. A composition according to claim 25 wherein $R_5$ is 2-methyl-1-propene.

27. A composition according to claim 26 wherein $R_1$, $R_2$, $R_3$ and $R_4$ are hydrogen.

28. A composition according to claim 18 wherein A=$(CH_2)_n$-phenyl where n=1–14.

29. A composition according to claim 28 wherein $R_5$ is 2-methyl-1-propene.

30. A composition according to claim 29 where $R_1$, $R_2$, $R_3$ and $R_4$ are H.

31. A composition according to claim 18 wherein A=cycloalkyl.

32. A composition according to claim 18 wherein A=cycloalkenyl.

33. A composition according to claim 18 wherein A=—$(CH_2)_n$13 COOH where n=1–19.

34. A composition according to claim 18 wherein A=—$(CH_2)_n$—$NH_2$ where n=1–20.

35. A method for treating mammals suffering from inflammation or pain to reduce said inflammation or pain, said method comprising:

administering to said mammal a pain reducing effective amount of an ether derivative of pseudopterosin having the structure:

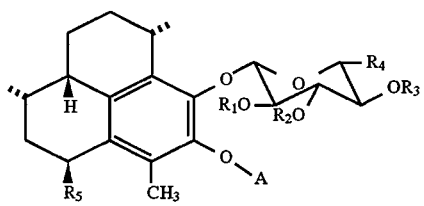
wherein A is an alkyl, aryl, hydroxyalkyl, cycloalkyl, cycloalkenyl, carboxylic acid, alkylamino or amide group having from 2 to 20 carbon atoms. $R_1$, $R_2$ and $R_3$ are hydrogen or acyl residue having from 1 to 6 carbon atoms, $R_5$ is a hydrogen or $CH_2OH$ and $R_5$ is an organo group having from 1 to 10 carbon atoms.
* * * * *